United States Patent [19]

Taubman et al.

[11] Patent Number: 5,686,075
[45] Date of Patent: Nov. 11, 1997

[54] SYNTHETIC PEPTIDE VACCINES FOR DENTAL CARIES

[75] Inventors: Martin A. Taubman, Newtonville; Daniel J. Smith, Natick, both of Mass.

[73] Assignee: Forsyth Dental Infirmary for Children, Boston, Mass.

[21] Appl. No.: 57,162

[22] Filed: Apr. 30, 1993

Related U.S. Application Data

[63] Continuation-in-part of Ser. No. 877,295, May 1, 1992, abandoned.
[51] Int. Cl.$^6$ .................................................. A61K 39/09
[52] U.S. Cl. .............................. 424/197.11; 124/185.1; 124/190.1; 124/193.1; 124/194.1; 530/324; 530/350
[58] Field of Search .......................... 424/88, 92, 185.1, 424/190.1, 193.1, 194.1, 197.11, 244.1; 530/350, 324, 325, 326

[56] References Cited

U.S. PATENT DOCUMENTS

| | | | |
|---|---|---|---|
| 4,150,116 | 4/1979 | Taubman et al. | 424/88 |
| 4,250,262 | 2/1981 | Taubman et al. | 435/193 |
| 4,438,200 | 3/1984 | Taubman et al. | 435/193 |
| 4,894,229 | 1/1990 | Polson et al. | 424/92 |

FOREIGN PATENT DOCUMENTS

| | | |
|---|---|---|
| 0328403 | 8/1989 | European Pat. Off. |
| WO91/07979 | 6/1991 | WIPO |

OTHER PUBLICATIONS

Ferretti et al., "Nucleotide Sequence of a Glucosyltransferase Gene from *Streptococcus sorbrinus* MFe28," *Journal of Bacteriology* 169(9): 4271–4278 (1987).

Banas et al., "Sequence Analysis of the Gene for the Glucan–Binding Protein of *Streptococcus mutans* Ingbritt," *Infection and Immunity*, 58(3): 667–673 (1990).

R.R.B. Russell et al., "Homology of Glucosyltransferase Gene and Protein Sequences from *Streptococcus sobrinus* and *Streptococcus mutans*," *J. Dent. Res.*, 67(3): 543–547 (1988, Mar.).

M.T. Dertzbaugh et al., "Cholera Toxin B–Subunit Fusion: Structural and Functional Analysis of the Chimeric Protein," *Infection and Immunity*, 58(1): 70–79 (1990, Jan.).

Taubman, M. et al., "T Cell Epitopes on Synthetic Peptides from the Glucan Binding and Catalytic Regions of *Mutants streptocci*", Abstract and poster presentation at IADR General Session, Glasgow, Scotland, Jul. 1–4, 1992 (abstract pub. *J. Dent. Res.* 71, p. 577, abstract #491 (1992)).

Ellis in Vaccines Chapter 29 Plutkin et al. Eds WB Saunders Co p. 573, 1988.

(List continued on next page.)

*Primary Examiner*—Lila Feisee
*Assistant Examiner*—Julie E. Reeves
*Attorney, Agent, or Firm*—Hamilton, Brook, Smith & Reynolds, P.C.

[57] ABSTRACT

Immunization of animals with a composition containing either an amino acid sequence from the catalytic domain of glucosyltransferase, an amino acid sequence from the glucan-binding region of glucosyltransferase or an amino acid sequence from the native surface domain of glucosyltransferase provoke antibody and T-cell immune responses to this enzyme. Since this enzyme has been implicated in the colonization of mutans streptococci on tooth surfaces, such immune responses are important for the prevention of dental caries. Multicomponent and multivalent compositions which include these amino acid sequences provide effective vaccine capabilities.

21 Claims, 1 Drawing Sheet

OTHER PUBLICATIONS

Taubman et al INfection and Immunity vol. 63 No. 8:3088–3093, Aug. 1995.

Smith et al Infection and Immunity vol. 55 No. 5 1274–1278, May 1987.

J.P. Tam, "Synthetic Peptide Vaccine Design: Synthesis and Properties of a High Density Multiple Antigenic Peptide System," *Proc. Nat'l Acad. Sci. USA*, 85: 5409–5413 (1988, Aug.).

T. Lehner et al., "Local Oral Immunization with Synthetic Peptides Induces a Dual Mucosal IgG and Salivery IgA Antibody Response and Prevents Colonization of *Streptococcus mutans*," *Immunology*, 67: 419–424 (1989).

Samith et al., "Immunological Characteristics of Synthetic Peptides Derived from Glucosyltransferase (GTF) Sequences . . . " Abstract and poster presentation for Cariology for the Nineties, Rochester, NY, Jun. 4–7, 1991.

Dertzbaugh et al., "Inhibition of *Streptococcus mutans* Glucosyltransferase Activity by Antiserum to a Subsequence Peptide," *Infection and Immunity*, 58(6): 1509–1513 (1990).

Arnon et al. (1992) FASEB J. vol. 6 pp. 3265–3274 "Structural Basis of Antigenic Specificity and Design of New Vaccines".

Smith et al (1993) Infect Immun 61(7): 2899–2905.

Abo et al (1991) J. Bact 173(3):989–996.

Smith et al (1991, Mar.) Published Abstract IADRI AADR, 1991 Apr.–Acapulco, Mexico.

Mooser et al (1991) J. Biol. Chem. 266(14):8916–8922.

Mosci et al (1989) Minerva Stomatal 38(3):379–388 (Abstract Only).

Wong et al (1990) Infect Immun 58(7):2165–2170.

Honda et al (1990) J. Gen. Microbiol. 136:2099–2105.

Shiroza et al (1987) J. Bact. 169(9) 4263–4207.

Ueda et al (1988) Gene 69: 101–109.

Mooser et al (1988) Infected Immun 56(4):880–884.

Hajishengallin et al (1989) Odontostomatol Proodos 43(4):315–321 (Abstract Only).

Schneerson et al (1984) Inf. Immun 45(3):582–591.

Gregory et al (1987) Infect. & Immun 55(10):2409–2415.

Smith et al (1987) Infect. Immun 55(11):2562–2569.

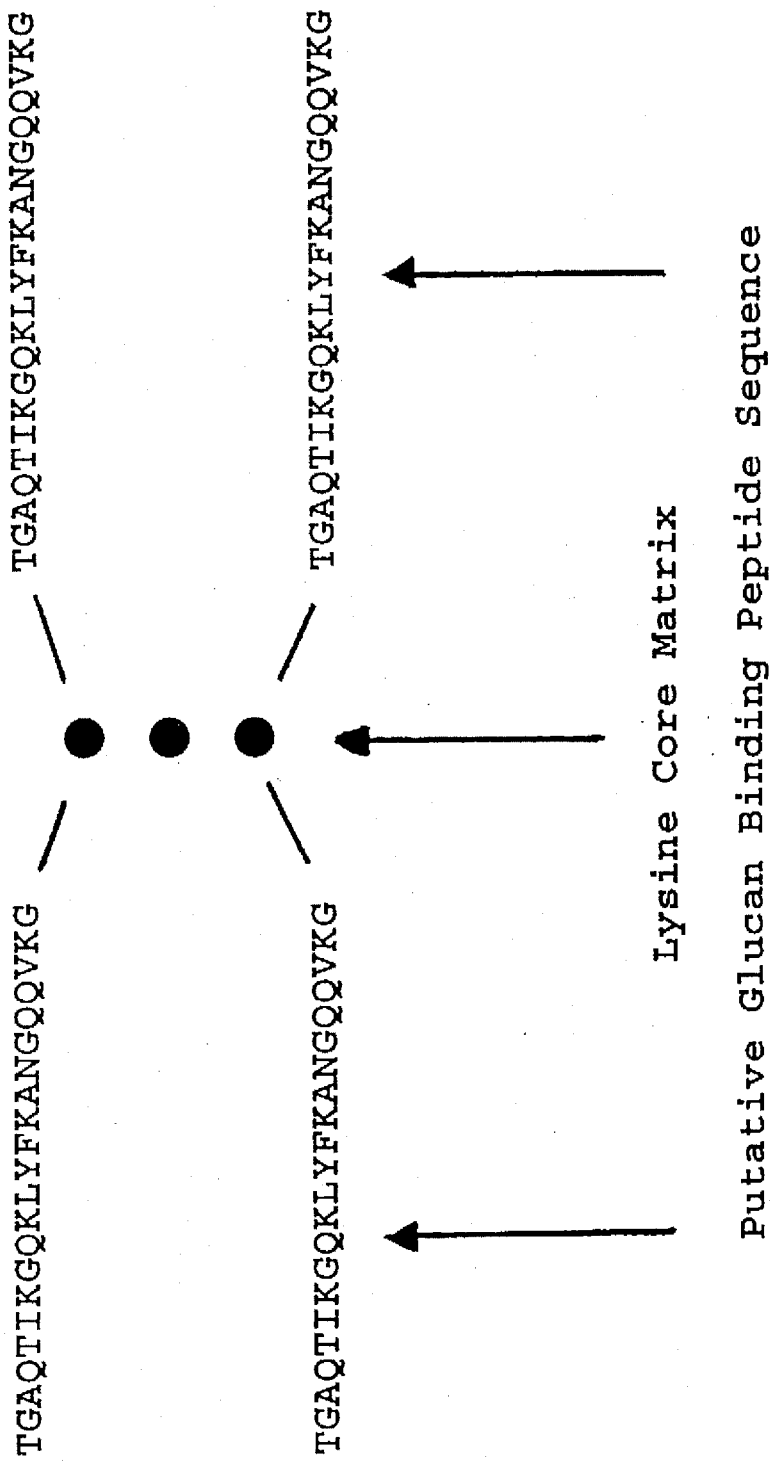

SYNTHETIC PEPTIDE VACCINES FOR DENTAL CARIES

RELATED APPLICATION

This application is a continuation-in-part of application Ser. No. 07/877,295, now abandoned, entitled "Synthetic Peptide Vaccines for Dental Caries" by Martin A. Taubman and Daniel J. Smith, filed May 1, 1992. The teachings of application Ser. No. 07/877,295 now abandoned, are incorporated herein by reference.

GOVERNMENT FUNDING

This invention was made with Government support under NIH grant no. DE-04733 awarded by the National Institutes of Health. The U.S. Government has certain rights in the invention.

BACKGROUND OF THE INVENTION

Mutans streptococci have been convincingly implicated in the initiation of dental caries in humans. The ability of these organisms to accumulate and colonize on the tooth surface has been associated with the synthesis of glucans from sucrose. These glucans are synthesized by constitutively secreted glucosyltransferase (GTF) enzymes. These enzymes have been considered as potential components of a dental caries vaccine, because of their role in the pathogenicity of mutans streptococci. Experiments in animal models and in humans have supported this potential. For example, glucosyltransferases from S. sobrinus and S. mutans species of the mutans streptococci have been demonstrated to elicit immune responses which are protective for experimental dental caries caused by infection with several mutans streptococcal species (Taubman and Smith, J. Immunol, 118:710, (1978); Smith and Taubman, Infect. Immunity, 21:843, (1978)). Oral and/or local administration of glucosyltransferases to humans has also been significantly correlated with the reduction of the ability of indigenous mutans streptococci to reaccumulate in the oral cavity (Smith and Taubman, Infect. Immunity, 55:2562, (1987); J. Clin. Immunol., 10:273, (1990)). Successful experimental applications of GTF-based vaccines have been associated with the appearance of mucosal (predominantly IgA) antibody alone, or with the combined appearance of mucosal and systemic (IgG) antibody. However, vaccines based on intact GTF have a variety of disadvantages such as the presence of inappropriate epitopes and excess molecular material that does not possess appropriate immunogenic features.

SUMMARY OF THE INVENTION

This invention pertains to vaccine compositions which elicit immune system responses in mammals to glucosyltransferase (GTF), an enzyme that is implicated in the formation of dental caries. Rather than using intact GTF as an immunizing agent, a vaccine prepared from particular immunogenic portions of GTF is desirable. These vaccine compositions are comprised of a peptide which consists essentially of at least one amino acid sequence of glucosyltransferase which is of sufficient length to raise an immune response in the mammal to whom it is administered. In preferred embodiments of the present invention, the amino acid sequence(s) used to elicit an immune response consists of all or a portion of the amino and sequence from the catalytic domain of glucosyltransferase, the glucan-binding domain of glucosyltransferase, the native surface domain of glucosyltransferase or a combination of these domains of glucosyltransferase. In particularly preferred embodiments of the present invention, the amino acid sequence is DANFDSIRVDAVDNVDADLLQI (SEQ ID NO: 1) or PLDKRSGLNPLIHNSLVDREVDDRE (SEQ ID NO: 2) of the catalytic domain, TGAQTIKGQKLYFKANGQQVKG (SEQ ID NO: 3) or DGKLRYYDANSGDQAFNKSV (SEQ ID NO: 4) of the glucan-binding domain, QWNGESEKPYDDHL (SEQ ID NO: 5) of the native glucosyltransferase surface domain or combinations of these sequences. In one embodiment, the vaccine composition comprises both an amino acid sequence of the catalytic domain of glucosyltransferase and an amino acid sequence of the glucan-binding domain of glucosyltransferase and each is of sufficient length to raise an immune response in a mammal to whom it is administered. In a particular embodiment, at least 2 peptides of glucosyltransferase are present and arranged on a peptidyl core matrix and each peptide consists of an amino acid sequence of glucosyltransferase of sufficient length to raise an immune response. In another embodiment, at least 2 peptides of glucosyltransferase and an additional immunologic component comprised of an amino acid sequence which is not an amino acid sequence of glucosyltransferase are present on the peptidyl core matrix. The amino acid sequences of glucosyltransferase used in the vaccine composition of the present invention, elicit both the production of antibodies and immunogen-recognizing T-cells causing interference with either the enzymatic or glucan-binding activity of glucosyltransferase resulting in reduction of colonization or accumulation of S. mutans strains and generating protective immunity against dental caries in mammals to whom the composition is administered. Thus, the present invention also pertains to a method of provoking an immune response to glucosyltransferase in mammals by administering to the mammal a peptide consisting of an amino acid sequence of glucosyltransferase of sufficient length which thereby provokes an immune response in the mammal to whom the peptide is administered. In a particular embodiment, the method of provoking an immune response involves interference with the enzymatic activity or glucan binding activity of glucosyltransferase. The present invention therefore provides a vaccine that is useful for preventing or halting progression of dental caries in a mammal to whom the vaccine is administered.

Development of a vaccine for dental caries that is constructed of synthetic peptides has several benefits. Using a vaccine composition comprised of 2 or more peptides wherein each peptide consists essentially of amino acid sequences of glucosyltransferase, one creates a multicomponent vaccine in which the concentration of epitopes of GTF required for antigen recognition and protective immune responses is maximized. Examples of sequences which are useful in a GTF-based synthetic vaccine include epitopes that correspond to critical GTF enzymatic functions. Inappropriate epitopes of glucosyltransferase are excluded, such as those that trigger suppressive immune responses or cross-react with host components. Synthetic peptide technology ultimately permits known effective T-cell epitgpes and sequences imparting enhanced adjuvanticity to be combined with epitopes that elicit protective responses. This technology can be extended to create multivalent vaccines by including the appropriate epitopes from several vaccine antigens in one synthetic macromolecule.

BRIEF DESCRIPTION OF THE FIGURE

The FIGURE is a diagrammatic representation of the tetravalent antigenic peptide structure used for immunization.

DETAILED DESCRIPTION OF THE INVENTION

The principal etiologic agents of the infectious disease, dental caries, are mutans streptococci. These oral pathogens infect the oral cavity during early childhood and normally remain associated with the host's dentition for life. Mutans streptococci must colonize and then accumulate on the tooth surface in sufficient numbers to achieve dissolution of the enamel. After the initial colonization by mutans streptococci on the tooth surface, the mutans streptococci produce glucosyltransferase (GTF), an enzyme which catalyzes the synthesis of glucans from sucrose. In addition, S. mutans express cell surface proteins which serve as glucan binding sites. Glucans mediate much of the subsequent accumulation of mutans streptococci on the tooth surface. This results in an increase in the numbers of potentially cariogenic bacteria in plaque. The metabolism of various saccharides by the accumulated bacterial mass results in excretion of significant amounts of lactic acid as a metabolic product, which causes demineralization when present in sufficient amount in close proximity to the tooth surface. This eventually results in a carious lesion.

The vaccine composition of the present invention is comprised of a peptide consisting essentially of at least one amino acid sequence of glucosyltransferase of sufficient length to raise an immune response against glucosyltransferase in a mammal to whom it is administered, thereby intercepting the cariogenic process. Glucosyltransferases of the mutans streptococci are particularly well-suited for application of synthetic vaccine technology for dental caries. The primary sequences of several mutans streptococcal GTFs have been deduced from DNA studies. Ferretti, J. J., et al., Infect. Imm., 56:1585–1588 (1988); Russell, R.R.B., et al., J. Dental Res., 67:543–547 (1988); Ueda, S., et al., Gene, 69:1101–1109 (1988). These DNA studies allow the application of algorithms which predict features which are associated with B or T cell epitopes. Garnier, J., et al., J. Mol. Biol., 120:97–120 (1978); Hopp, T. P. et al., Proc. Natl. Acad. Sci., 78 (1981); Rothbard, J. B., et al., EMBO, 7:93–100 (1988). Although GTFs are large molecules, they function through a few discrete sites, which include the catalytic and glucan-binding sites. Very recently, primary sequences have been identified which provisionally include these sites. Mooser, G., et al., J. Dental Res., 69:325 (1990); Russell, R.R.B., et al., J. Dental Res., 67:543–547 (1988). This permits the design of synthetic peptides for a caries vaccine which contain epitopes eliciting the production of T cells and B cells which interfere with glucosyltransferase function.

In one embodiment of the vaccine composition of the present invention, the peptide, consisting of at least one amino acid sequence of glucosyltransferase used to elicit an immune response, is comprised of at least one amino acid sequence of glucosyltransferase which is associated with a function of the glucosyltransferase molecule. Thus, the peptide consists of at least one amino acid sequence from all or a portion of the amino acid sequence of the catalytic domain or all or a portion of the amino acid sequence of the glucan binding domain of GTF. In a particular embodiment, the amino acid sequence DANFDSIRVDAVDN-VDADLLQI (SEQ ID NO: 1) or PLDKRSGLNPLIHNSLV-DREVDDRE (SEQ ID NO: 2) of the catalytic domain of GTF, or TGAQTIKGQKLYFKANGQQVKG (SEQ ID NO: 3) or DGKLRYYDANSGDQAFNKSV (SEQ ID NO: 4) of the glucan-binding domain of GTF can be used. Synthetic vaccine design containing peptides consisting of an amino acid sequence from the catalytic domain of GTF (CAT-pep) and an amino acid sequence from the glucan binding domain of GTF (GLUa-pep) is described in Example 1. In a particular embodiment, both an amino acid sequence of all or a portion of the catalytic domain and an amino acid sequence from all or a portion of the glucan-binding domain of glucosyltransferase are present. Each amino acid sequence of glucosyltransferase is of sufficient length to raise an immune response in a mammal to whom the vaccine composition is administered. In another embodiment, the peptide, comprised of at least one amino acid sequence of glucosyltransferase, consists of all or a portion of an amino acid sequence which exists on the native surface domain of glucosyltransferase. In a particular embodiment, the amino acid sequence QWNGESEKPYDDHL (SEQ ID NO: 5) of the native glucosyltransferase surface domain can be used.

Those skilled in the art will be able to determine other amino acid sequences of glucosyltransferase which can be used as an immunologic component in the vaccine composition of the present invention using routine experimentation.

Although the vaccine composition of the present invention can contain one peptide consisting of at least one amino acid sequence of GTF, preferred embodiments of the vaccine composition of the present invention consist of at least 2 peptides containing an amino acid sequence of GTF in which each amino acid sequence is of sufficient length to raise an immune response. In one embodiment, both an amino acid sequence of the catalytic domain and of the glucan-binding domain of glucosyltransferase are present and each amino acid sequence is of sufficient length to raise an immune response in a mammal to whom it is administered. In another embodiment, 2 or more peptides containing an amino acid sequence of all or a portion of the catalytic domain, the glucan binding domain, or the native surface domain of GTF are present in the vaccine composition. In another embodiment, 2 or more peptides containing a combination of amino acid sequences of all or a portion of the catalytic domain, the glucan binding domain, the native surface domain and other immunologic domains of GTF are present, producing a multicomponent vaccine composition. In a further embodiment, 2 or more peptides, containing all or a portion of an amino acid sequence of the catalytic domain, the glucan binding domain, the native surface domain and other immunologic domains of GTF, as well as additional immunologic components of non-GTF origin which enhance adjuvanticity or produce an immunogenic response against other infectious agents, are present in the vaccine composition. In particular embodiments, using the vaccine composition of the present invention, the additional immunologic components can be amino acid sequences selected from immunologic domains of infectious diseases such as, but not limited to, diphtheria, pertussis, tetanus, measles and polio vaccine, resulting in a multivalent vaccine producing protection against greater than one infectious disease or agent. Ultimately, a multivalent vaccine can be produced which incorporates relevant protective epitopes and appropriate adjuvant sequences targeting early childhood infections.

The peptides present in the vaccine composition of the present invention may be designed in a number of ways to enhance immunogenicity. In one embodiment in which the vaccine composition contains one or more peptides, the peptide(s) is conjugated to a known protein, (such as tetanus toxoid) or a carrier (such as a synthetic polymer carrier) to give a macromolecular structure to the vaccine which thereby enhances immunogenicity. In a preferred embodiment in which the vaccine composition contains at least 2 peptides, the peptides are synthesized and covalently attached to a peptidyl core matrix to yield a macromolecule with a high density of peptides in a single structure. Each peptide in such a structure consists essentially of amino acid sequences of GTF of sufficient length to raise an immune response in the mammal to whom it is administered. The peptidyl core matrix can consist of amino acids such as lysine, arginine and histidine. In particular, at least 2 peptides are synthesized on a core matrix of at least one lysine to yield a macromolecular vaccine composition. Particularly, at least 2 peptides are synthesized on a core matrix of 3 lysines. In a preferred embodiment, a vaccine composition is designed in which four peptides of the present invention are synthesized and covalently attached to a core matrix of 3 lysines yielding a radially branched peptide with four dendritic arms. In this embodiment, the four peptides present can be the same or different. This macromolecular vaccine structure is described in Example 1 using 4 peptides from the catalytic domain of GTF and demonstrated in the FIGURE using 4 peptides from the glucan binding domain of GTF.

Those skilled in the art will be able to determine other variations of synthesizing and covalently attaching vaccine compositions of the present invention to a peptidyl core matrix by employing routine experimentation.

The immune response elicited by the synthetic peptides of the vaccine composition of the present invention comprises a B cell response and/or a T cell response. The B cell response is associated with the appearance of mucosal antibody which is predominantly IgA and systemic antibody which is predominantly IgG. As demonstrated in Example 2, both the CAT-pep peptide and the GLUa-pep peptide synthesized in Example 1 elicit a B cell response in vivo to GTF. Further, the GLUa peptide also elicits a T cell response in vivo to GTF.

The present invention further relates to a method of provoking an immune response to glucosyltransferase in mammals by administering a peptide consisting essentially of an amino acid sequence of glucosyltransferase of sufficient length to raise an immune response in a mammal. Preferably, the immune response results in interference with the enzymatic or glucan binding activity of glucosyltransferase in mammals after administration of the vaccine composition. The immune response elicited by the method of the present invention results in reduction of the colonization or accumulation of mutans streptococcal strains in the mammal to whom the vaccine is administered.

The vaccine composition of the present invention can be administered to any mammal in which the prevention of dental caries is desired. The present invention provides a vaccine that is useful for preventing or halting the progression of dental caries in a mammal to whom the vaccine is administered.

In the method of the present invention of provoking an immune response to glucosyltransferase, mammals in which an immune response to glucosyltransferase is desired are given the vaccine composition described herein. The vaccine composition can be included in a formulation which is administered to an individual being treated; such a formulation can also include a physiologically compatible carrier (e.g., a physiological buffer), stabilizers, flavorants, adjuvants and other components. The vaccine can be administered by a variety of routes (e.g., parenterally, intravenously) and the components of the formulation will be selected accordingly. The amount to be administered and the frequency of administration can be determined empirically and will take into consideration the age and size of the mammal being treated and the stage of the dental caries disease (e.g., prior to colonization of mutans streptococci, soon after colonization of mutans streptococci or in later stages of colonization).

The present invention is illustrated by the following Examples, which are not intended to be limiting in any way.

EXAMPLE 1

Synthetic Vaccine Design

CAT-pep: It was presumed that antibody-mediated interference with the catalytic activity of GTF will significantly reduce the colonization and/or accumulation potential of mutans streptococci. A synthetic peptide which includes amino acids 5–13 of SEQ ID NO: 1 of the catalytic region of GTF was presumed to elicit antibody with these characteristics. Therefore, the location of the nonapeptide within published sequences of S. sobrinus (Ferretti et al., J. Dent. Res. 67:541, (1988)) was identified. Since immunogenicity of a peptide usually requires that the host recognizes at least two epitopes of at least 5–7 amino acids within a structure, a larger 22 amino acid sequence was synthesized which included the target aspattic acid. This sequence is shown in Table 1 and is referred to as CAT-pep.

TABLE 1

| S. sobrinus GTFI | DANFDSIRVDAVDNVDADLLQI (SEQ ID NO: 1) |
| S. mutans GTFB | DANFDSIRVDAVDNVDADLLQI (SEQ ID NO: 1) |

Since this sequence is identical in GTF from S. mutans, antibody formed to CAT-pep would very likely cross-react with GTF from S. mutans. Furthermore, all the amino acid residues within the catalytic active site peptide amino acids 5–13 of SEQ. ID NO: 1 are either identical or conserved in the respective deduced sequences of S. sobrinus GTFs that make either insoluble or soluble glucan. These homologies are significant in vaccine design since S. mutans strains are the mutans streptococcal strains which most frequently colonize humans.

An additional feature was incorporated into the design of the CAT-synthetic peptide to enhance further its potential immunogenicity. This involved synthesis of the peptide on a core matrix of lysine to yield a macromolecule with a high density of the CAT-pep epitopes in a single structure. Specifically, four of the 22 amino acid CAT peptides were synthesized on a core matrix of three lysines yielding a radially branched CAT-pep as four dendritic arms, as shown for the GLUa-pep in FIG. 1.

GLUa-pep: There is evidence for a second functional domain on the GTF molecule. Structural (Ferretti et al., J. Bact. 169:4271, (1987)) and biochemical (Mooser & Wong, Infect. Immunity, 56:880, (1988); (Wong et al., Infect. Immunity, 58:2165, (1990)) studies suggest that a separate glucan-binding region(s) exists in the C-terminal third of the GTF molecule. Analysis of the primary structure of deduced sequences of GTFs from both S. mutans and S. sobrinus reveal multiple repeating amino acid regions that have been theoretically associated with the glucan binding properties of GTF. This hypothesis is supported by high affinity binding of glucan by tryptic fragments from this area of the molecule (Wong et al., Infect. Immunity, 58:2165, (1990)) and by the amino acid homology of these regions with repeating sequences in an independent streptococcal protein with glucan-binding characteristics (Banas et al., Infect. Immunity, 58:667, (1990)). A sequence was selected that was derived from one of the repeating regions (residues 1293–1328) for synthetic peptide preparation, based on homology with the other repeating regions of S. sobrinus GTF, homology with corresponding sequences in S. mutans GTF, hydrophilicity, and secondary structure. This sequence is referred to as GLUa-pep. The core matrix synthesis procedure used for the CAT-pep was also used to synthesize a four chain GLUa-pep peptide structure with a lysine backbone (FIG. 1).

EXAMPLE 2

Immunogenicity of the Synthetic Peptides

The immunogenicities of the GLUa and CAT synthetic peptides were measured by injecting Sprague-Dawley rats with 50 ug of the respective peptide (N=3 rats/peptide). Injections were given intramuscularly and subcutaneously. On the first injection (day 0) each peptide was incorporated into completed Freund adjuvant. On the three subsequent injections, peptide was incorporated into incomplete Freund adjuvant. Other rats were injected with 15 ug of GTF from S. sobrinus or S. mutans. Control rats were sham-injected with buffer and adjuvant alone over the same schedule. All rats were bled and salivated on day 80 for the purpose of measuring antibody levels. Also, the spleens were taken at this time to measure levels of lymphocyte blastogenesis, using the respective peptides.

ELISA: Both peptides were exceptionally immunogenic. Each elicited vigorous serum IgG responses to the injected antigen. The sera of rats injected with the GLUa-pep could be shown to react with bound GLUa-pep at a reciprocal titer of >50,000. Sera from rats injected with the CAT-pep or GTF from S. sobrinus did not demonstrate significant reaction with the GLUa-pep by this technique.

The CAT-synthetic peptide also elicited vigorous responses in the respectively injected rats. Reaction with the homologous synthetic peptide was observed to occur at reciprocal serum dilutions greater than 10,000. Antisera from rats injected with GTF from S. mutans also reacted with the CAT-pep at reciprocal dilutions greater than 1,000, suggesting that common epitopes exist on the intact GTF and CAT-synthetic peptide. Essentially no reaction was observed with antisera from rats immunized with GTF from S. sobrinus or the GLUa-pep by this technique.

It was found that GTF from S. sobrinus elicited a serum IgG antibody response which reacted with the homologous antigen at reciprocal dilutions greater than $10^6$, and at dilutions greater than $10^4$ with the heterologous GTF. GTF from S. mutans elicited vigorous reactive and crossreactive responses with both intact GTF enzymes. Importantly, the antisera from rats injected with the CAT- or GLUa-synthetic peptides also reacted with both intact GTF antigens, albeit at a lower dilution (1:800–1:1600). These crossreactions strengthened the evidence for shared epitopes between both synthetic peptides and intact GTF. The observation that rat anti-peptide antisera reacted with GTF from both S. sobrinus and S. mutans GTFs indicated that synthetic peptide epitopes were shared between these mutans streptococcal GTFs and had the potential to form the basis of a dental caries vaccine in mammals effective against prominent human strains.

WESTERN BLOT: Western blot techniques also provided evidence that antibody to epitopes on intact GTF could be elicited by injection with either synthetic peptide. Antisera from CAT-pep and GLUa-pep injected rats were reacted with GTF in the following manner. Glucosyltransferase from S. sobrinus strain 6715 was electrophoresed in SDS 7% polyacrylamide gels, together with prestained standards. After electrophoresis, proteins from the gels were transferred to nitrocellulose. Reactivity of the rat antisera to the synthetic peptide and to intact GTF antigens was measured by exposing each antiserum to the electrophoresed GTF and developing for rat IgG antibody. Rat antisera to the intact GTF (S. sobrinus) reacted strongly, and antisera to intact S. mutans GTF reacted moderately, to S. sobrinus GTF bands in the 150–165 kD range. Antisera to both the CAT and GLUa-synthetic peptides also formed bands which were visible in this range. Although these bands were much less intense than those formed with the rat antisera to GTF, the reactions indicated the presence of similar epitopes on GTF and the synthetic peptides.

LYMPHOCYTE BLASTOGENESIS: In order to evaluate the T-cell epitopes of the respective peptides used to immunize rats, spleens were removed from each animal and single cell suspensions were prepared and lymphocytes were isolated by gradient centrifugation. Cells ($5\times10^5$) were reacted with either no additive (control), CAT-peptide, polylysine peptide, S. sobrinus GTF or S. mutans GTF for 5 days in culture. Tritiated thymidine was added for the final 16 hours of culture. The positive findings are summarized in Table 2.

TABLE 2

| | | Positive Responses of Animals Sensitized with Peptides Test Antigen (Mean Tritium CPM ± SE) | | | |
|---|---|---|---|---|---|
| Immunizing Antigen | (n) | Control (n = 16–22) | CAT-Pep | GLUa-Pep | GTF S. sobrinus | GTF S. mutans |
| CAT-Pep | 3 | 5304 ± 294 | 9305 ± 944 | NS* | NS | NS |
| GLUa-Pep | 3 | 2022 ± 153 | NS | NS | 3733 ± 371 | NS |
| | | 2046 ± 205 | NS | NS | 3894 ± 841 | NS |
| S. sobrinus GTF | 2 | 3839 ± 288 | NS | 2013 ± 175 | 18555 ± 2791 | NS |
| | | 2120 ± 275 | NS | 9116 ± 984 | 9903 ± 1510 | NS |
| S. mutans GTF | 1 | 474 ± 31 | NS | NS | NS | 723 ± 59 |

*NS = $^3$H incorporation not significantly greater than in controls.

Cells from 1 to 3 animals immunized with CAT-pep Showed a highly significant elevated stimulation with the homologous CAT-pep. Cells from 2 of 3 animals immunized with GLUa-pep showed highly significant reactivity with S. sobrinus GTF. Cells from animals immunized with S. sobrinus GTF demonstrated significant stimulation with GLUa-pep and with the homologous GTF (p<0.01). Cells from the 1 animal immunized with S. mutans GTF only showed stimulation with the homologous GTF.

In summary, the results indicate that: 1) Cells from animals immunized with CAT peptide will proliferate to a high concentration of CAT peptide. 2) Cells of animals immunized with GLUa peptide will react with S. sobrinus GTF. 3) Cells from animals sensitized to S. sobrinus GTF react with S. sobrinus GTF and GLUa peptide. 4) Cells from an animal immunized with S. mutans GTF reacted only with the homologous GTF collectively, these data indicate that T cell epitopes are present on the Glua-synthetic peptide, as predicted from sequence patterns common to T cell epitopes (Rothbard & Taylor, EMBO 7:93, 1988)). Also, these experiments reveal that T cell epitopes, that are cross-reactive with those on the synthetic peptides, are present on the intact GTF from S. sobrinus.

In addition, since both the CAT peptide and the GLUa peptide synthesized on a core matrix of lysine were each shown to elicit an immune response to glucosyltransferase in mammals to whom it was administered, a combination of these peptides synthesized on a core matrix of lysine will also elicit such an immune response. Ultimately, synthetic peptide technology should permit the combination, on a core matrix of 3 or more lysines, of the epitopes of glucosyltransferase which elicit a protective response against dental caries with epitopes which impart enhanced adjuvanticity in the mammal to whom it is administered. Therefore, administration of a series of systemic injections of vaccine containing synthetic peptide epitopes of GTF should result in long lasting protection from dental caries.

EXAMPLE 3

Reactivity of T and B Lymphocytes to Glucosyltransferase (GTF) in Humans

The T lymphocyte (proliferation) and B (antibody) lymphocyte responses in humans to the subject peptide constructs were investigated. Blood was taken from 14 subjects with decayed, missing and filled tooth surfaces (DMFS) from ages 2 to 37 years and serum (plasma) antibodies and lymphocyte proliferation were examined.

SERUM ANTIBODY: The IgG antibody in plasma of these individuals to GTFss (S. sobrinus), GTFsm (S. mutans), CAT and GLUa was measured by ELISA techniques. The antibody levels to each of these antigens were ranked, with 1 being the highest. Although antibody levels were ranked, all subjects appeared to demonstrate some level of antibody to the peptides which suggests that B cell epitopes recognizable by humans were probably present on the CAT and GLUa peptides (Table 3).

TABLE 3

Relationship of Serum Antibody Level to Mononuclear Cell Stimulation

| Subject | GTFss[1] | GTFsm[2] | CAT[3] | GLUa[4] | CON A[5] | GTFss[5] | CAT[5] | GLUa[5] |
|---|---|---|---|---|---|---|---|---|
| CI | 9 | 4 | 2 | 2 | 47 | 3.0 | 5.5 | 6.1 |
| CH | 11 | 8 | 14 | 10 | 115 | 2.5 | — | 2.8 |
| DS | 7 | 6 | 5 | 5 | 66 | — | — | — |
| JD | 6 | 10 | 13 | 8 | 46 | 2.3 | — | — |
| HA | 3 | 14 | 11 | 13 | 37 | 2.5 | — | 2.4 |
| MT | 14 | 7 | 3 | 4 | 16 | 2.3 | — | 3.5 |
| WK | 12 | 2 | 6 | 3 | 64 | — | — | — |
| HS | 4 | 5 | 1 | 1 | 64 | — | — | — |
| JS | 8 | 9 | 8 | 11 | 50 | — | — | — |
| SS | 10 | 12 | 10 | 9 | 130 | — | — | — |
| OT | 1 | 1 | 4 | 6 | 106 | — | — | — |
| TY | 2 | 3 | 9 | 12 | 106 | 2..5 | — | 3.5 |
| XL | 5 | 13 | 7 | 7 | 40 | 2.2 | — | — |
| ZS | 13 | 11 | 12 | 4 | 32 | — | — | — |

[1]Rank 1 = 100 EU (ELISA Units); 4 = 9.4 EU.
[2]1 = 100 EU; 14 = 4.7 EU.
[3]1 = 100 EU; 14 = 4.5 EU.
[4]1 = 100 EU; 14 = 18.5 EU.
[5]Stimulation Index (SI) = Stimulated cpm/control cpm (Mean = 480 ± 109); SI shown significant at least at $p < 0.05$; — = SI < 2.2, Not significant.

LYMPHOCYTE BLASTOGENIC RESPONSES: The ability of these human peripheral blood T lymphocytes to recognize the subject peptides was also investigated (Table 3). Peripheral blood lymphocytes were prepared by centrifugation into Ficoll Histopaque. The mononuclear cells from 14 individuals (7F, 7M) aged 22–58 years were examined for proliferative response to concanavalin A, CAT, GLUa, poly-lysine, GTFss and GTFsm. Responses to GLUa and CAT and to S. mutans GTF were dose dependent with no detectable responses to poly-1-lysine as a control peptide. Seven of 14 subjects showed proliferation to GTFss, and 5 of these 7 individuals showed significant proliferative responses to GLUa. Only 1 subject demonstrated a proliferative response to CAT. Interestingly, those individuals with the highest antibody responses did not show lymphocyte proliferation to CAT, GLUa or GTF.

SEPARATION OF T CELL SUBSETS: This procedure was performed on the peripheral blood monocytic cells (PBMC) of 5 of the 14 previously tested individuals by removal of monocyte/macrophages and B cells on nylon wool and by negative panning on an anti-CD8 monoclonal antibody coated flask. Nonadherent cells were taken as CD4+ cells. The responses of the separated cells are shown in Table 4.

TABLE 4

Response of Separated T Cell Populations (CD4+ cells)

| Subject | Response of Mononuclear Cells* | GTFss | CAT | GLUa |
|---------|-------------------------------|--------|-----|-------|
| MT      | +                             | 2.7**  | —   | 8.1** |
| OT      | —                             | 4.9**  | —   | —     |
| HS      | —                             | —      | —   | —     |
| TY      | +                             | —      | —   | 2.5***|
| CI      | +                             | —      | —   | —     |

*Proliferative response of unseparated PB mononuclear cells to GTFss.
**SI statistically significant, at least $p < 0.05$. (Control CPM = $610 \pm 297$).
***Response of CD8+ cells.

Of the 5 subjects, 3 showed response to GTF and/or GLUa, while 1 responded to GTF and GLUa and 1 each responded to either GTF or GLUa. No T cell response to CAT was observed.

Fifty percent of the individuals tested showed elevated proliferative responses to GTFss. Only those individuals who responded to GTFss showed any response to the CAT or GLUa peptides. Only 1 of 14 individuals showed significant response to CAT while 5 of the 14 individuals tested showed significant proliferation to GLUa. There appeared to be no relationship between antibody response ranking in the group and the ability of the host peripheral blood lymphocytes to proliferate in response to either GTFss or GLUa. In fact, the 2 individuals with the highest levels of antibody did not show significant proliferation. Separation of the lymphocyte subsets indicated that the T cell reactivity resided predominantly in the CD4+population. However, one individual did show proliferative response in the CD8+ lymphocyte populations.

These combined observations support the presence of T cell epitopes and the possible existence of shared epitopes between CAT and GLUa and intact mutans streptococcal GTF. T cell epitopes do not appear to be present on the CAT-peptide but are present on the GLUa peptide. These findings demonstrate that individuals with the highest antibody levels do not necessarily have elevated lymphocyte proliferative responses to the same antigens but that B cell epitopes probably exist on both the CAT and GLUa peptides.

Equivalents

Those skilled in the art will recognize or be able to ascertain using no more than routine experimentation, many equivalents to the specific embodiments of the invention described herein. Such equivalents are intended to be encompassed in the scope of the following claims.

---

We claim:

1. An immunogenic composition comprising a peptide consisting of at least one amino acid sequence selected from the group consisting of:
   a) DGKLRYYDANSGDQAFNKSV (SEQ ID NO: 4), and
   b) PLDKRSGLNPLIHNSLVDREVDDRE (SEQ ID NO: 2); and a physiologically compatible carrier.

2. An immunogenic composition comprising at least two peptides, wherein at feast one peptide consists of an amino acid sequence of either DANFDSIRVDAVDNVDADLLQI (SEQ ID NO: 1) or PLDKRSGLNPLIHNSLVDREVDDRE (SEQ ID NO: 2) where both sequences are of the catalytic domain of streptococcal glucosyltransferase, and at least one peptide consists of an amino acid sequence of either TGAQTIKGQKLYFKANGQQVKG (SEQ ID NO: 3) or DGKLRYYDANSGDQAFNKSV (SEQ ID NO: 4) where both sequences are of the glucan-binding domain of streptococcal glucosyltransferase, and a physiologically compatible carrier.

3. An immunogenic composition of claim 2 where 2 or more of said peptides of the streptococcal glucosyltransferase protein are present and attached to a core matrix of 3 or more lysines.

4. The immunogenic composition of claim 1 wherein said composition induces in a mammal an immune response that is both a B cell response and a T cell response.

5. The immunogenic composition of claim 4 wherein the B cell immune response produces antibodies of the IgG or the IgA isotype.

6. An immunogenic composition comprising at least two peptides of a streptococcal glucosyltransferase protein covalently attached to a lysine core matrix, wherein each peptide consists of an amino acid sequence selected from the group consisting of:
   a) DANFDSIRVDAVDNVDADLLQI (SEQ ID NO: 1),
   b) TGAQTIKGQKLYFKANGQQVKG (SEQ ID NO: 3),
   c) DGKLRYYDANSGDQAFNKSV (SEQ ID NO: 4),
   d) QWNGESEKPYDDHL (SEQ ID NO: 5), and
   e) PLDKRSGLNPLIHNSLVDREVDDRE (SEQ ID NO: 2); and
   a physiologically compatible carrier.

7. The immunogenic composition of claim 6 having at least one additional immunologic component, which produces an immunogenic response against an infectious organism, covalently attached to said lysine core matrix, wherein said additional immunogenic component is a peptide comprising an amino acid sequence from an immunologic domain selected from the group consisting of diphtheria, pertussis, tetanus and measles.

8. The immunogenic composition of claim 6 wherein the lysine core matrix consists of at least three lysines.

9. The immunogenic composition of claim 6 wherein said composition induces in a mammal an immune response that is a B cell response, a T cell response or both a B cell response and a T cell response.

10. The immunogenic composition of claim 9 wherein both the B cell response and T cell response are elicited by the same amino acid sequence.

11. The immunogenic composition of claim 10 wherein the B cell immune response produces antibodies of the IgG or the IgA isotype.

12. An immunogenic composition of claim 6 comprising 4 peptides, where
a) the 4 peptides are the same or different;
b) each peptide consists of an amino acid sequence selected from the group consisting of DANFDSIRV-DAVDNVDADLLQI (SEQ ID NO: 1), PLDKRSGLN-PLIHNSLVDREVDDRE (SEQ ID NO: 2) where both sequences are of the catalytic domain of streptococcal glucosyltransferase, the amino acid sequence DGKL-RYYDANSGDQAFNKSV (SEQ ID NO: 4) of the glucan binding domain of streptococcal glucosyltransferase, and the amino acid sequence QWNGESEKPYDDHL (SEQ ID NO: 5) of the native streptoeoecal glucosyltransferase surface domain; and
c) the 4 peptides are attached to a core matrix of 3 lysines.

13. An immunogenic composition of claim 12 wherein said composition induces in a mammal an immune response that results in the reduction of the colonization or accumulation of mutans streptococcal strains in a mammal to whom the immunogenic composition is administered.

14. An immunogenic composition comprising a peptide consisting of an amino acid sequence of PLDKRSGLNP-LIHNSLVDREVDDRE (SEQ ID NO: 2) and a physiologically compatible carrier.

15. A method of interfering with the enzymatic activity of streptococcal glucosyltransferase in a mammal comprising the administration of a peptide consisting of an amino acid sequence of PLDKRSGLNPLIHNSLVDREVDDRE (SEQ ID NO: 2) to a mammal in a manner that raises an immune response in the mammal, thereby interfering with the enzymatic activity of streptococcal glucosyltransferase in the mammal.

16. A method of provoking an immune response to streptococcal glucosyltransferase in a mammal comprising the administration of a peptide consisting of an amino acid sequence of either PLDKRSGLNPLIHNSLVDREVDDRE (SEQ ID NO: 2) or DGKLRYYDANSGDQAFNKSV (SEQ ID NO: 4) in a manner that raises an immune response in the mammal.

17. The method of claim 16 wherein said immune response results in reduction of the colonization or accumulation of mutans, streptococcal strains in the mammal to whom the peptide is administered.

18. An immunogenic composition comprising a peptide consisting of an amino acid sequence of DGKLRYYDANS-GDQAFNKSV (SEQ ID NO: 4) and a physiologically compatible carrier.

19. A method of interfering with the glucan-binding activity of streptococcal glucosyltransferase in a mammal comprising the administration of a peptide consisting of an amino acid sequence of DGKLRYYDANSGDQAFNKSV (SEQ ID NO: 4) in a manner that induces a response which thereby interferes with the glucan-binding activity of streptococcal glucosyltransferase in the mammal.

20. An immunogenic composition comprising at least two peptides covalently attached to at least one additional immunologic component which produces an immunogenic response against an infectious organism, wherein each peptide is selected from the group consisting of:
a) DANFDSIRVDAVDNVDADLLQI (SEQ ID NO: 1);
b) PLDKRSGLNPLIHNSLVDREVDDRE (SEQ ID NO: 2);
c) TGAQTIKGQKLYFKANGQQVKG (SEQ ID NO: 3);
d) DGKLRYYDANSGDQAFNKSV (SEQ ID NO: 4); and
e) QWNGESEKPYDDHL (SEQ ID NO: 5); and a physiologically compatible carrier, wherein said additional immunologic component is a peptide comprising an amino acid sequence from an immunologic domain selected from the group consisting of diphtheria, pertussis, tetanus and measles.

21. An immunogenic composition comprising a peptide covalently attached to at least one additional immunologic component which produces an immunogenic response against an infectious organism, wherein said peptide is selected from the group consisting of:
a) DANFDSIRVDAVDNVDADLLQI (SEQ ID NO: 1);
b) PLDKRSGLNPLIHNSLVDREVDDRE (SEQ ID NO: 2);
c) TGAQTIKGQKLYFKANGQQVKG (SEQ ID NO: 3);
d) DGKLRYYDANSGDQAFNKSV (SEQ ID NO: 4); and
e) QWNGESEKPYDDHL (SEQ ID NO: 5); and a physiologically compatible carrier, wherein said additional immunologic component is a peptide comprising an amino acid sequence from an immunologic domain selected from the group consisting of diphtheria, pertussis, tetanus and measles.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Asp Ala Asn Phe Asp Ser Ile Arg Val Asp Ala Val Asp Asn Val Asp
 1               5                  10                      15
Ala Asp Leu Leu Gln Ile
                20
```

( 2 ) INFORMATION FOR SEQ ID NO:2:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Pro Leu Asp Lys Arg Ser Gly Leu Asn Pro Leu Ile His Asn Ser Leu
 1               5                  10                      15
Val Asp Arg Glu Val Asp Asp Arg Glu
                20              25
```

( 2 ) INFORMATION FOR SEQ ID NO:3:

( i ) SEQUENCE CHARACTERISTICS:
   ( A ) LENGTH: 22 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:3:

Thr Gly Ala Gln Thr Ile Lys Gly Gln Lys Leu Tyr Phe Lys Ala Asn
1               5                   10                  15

Gly Gln Gln Val Lys Gly
                20

( 2 ) INFORMATION FOR SEQ ID NO:4:

( i ) SEQUENCE CHARACTERISTICS:
   ( A ) LENGTH: 20 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:4:

Asp Gly Lys Leu Arg Tyr Tyr Asp Ala Asn Ser Gly Asp Gln Ala Phe
1               5                   10                  15

Asn Lys Ser Val
                20

( 2 ) INFORMATION FOR SEQ ID NO:5:

( i ) SEQUENCE CHARACTERISTICS:
   ( A ) LENGTH: 14 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:5:

Gln Trp Asn Gly Glu Ser Glu Lys Pro Tyr Asp Asp His Leu
1               5                   10